US012691054B2

(12) United States Patent
Lan et al.

(10) Patent No.: US 12,691,054 B2
(45) Date of Patent: Jul. 28, 2026

(54) SILICONE-(METH)ACRYLATE COPOLYMER AND METHODS FOR ITS PREPARATION AND USE IN PERSONAL CARE COMPOSITIONS

(71) Applicants: Dow Silicones Corporation, Midland, MI (US); DOW GLOBAL TECHNOLOGIES LLC, Midland, MI (US); Rohm and Haas Company, Collegeville, PA (US)

(72) Inventors: Tian Lan, Langhorne, PA (US); Ligeng Yin, Collegeville, PA (US); Lu Bai, Novi, MI (US); Fanwen Zeng, Audubon, PA (US); Jennifer Koenig, Lansdale, PA (US); Rosalind Toth, King of Prussia, PA (US); Meng Jing, Collegeville, PA (US); Michaeleen L. Pacholski, Collegeville, PA (US); Nanguo Liu, Midland, MI (US)

(73) Assignees: Dow Silicones Corporation, Midland, MI (US); Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 519 days.

(21) Appl. No.: 18/004,939

(22) PCT Filed: Oct. 5, 2021

(86) PCT No.: PCT/US2021/053523

§ 371 (c)(1),
(2) Date: Jan. 10, 2023

(87) PCT Pub. No.: WO2022/093497

PCT Pub. Date: May 5, 2022

(65) Prior Publication Data

US 2023/0240971 A1 Aug. 3, 2023

Related U.S. Application Data

(60) Provisional application No. 63/106,506, filed on Oct. 28, 2020.

(51) Int. Cl.

| | |
|---|---|
| ***A61K 8/893*** | (2006.01) |
| ***A61Q 1/12*** | (2006.01) |
| ***C08F 220/18*** | (2006.01) |
| ***C08F 230/08*** | (2006.01) |

(52) U.S. Cl.

CPC ................ *A61K 8/893* (2013.01); *A61Q 1/12* (2013.01); *C08F 220/1802* (2020.02); *C08F 220/1811* (2020.02); *C08F 230/085* (2020.02); *A61K 2800/43* (2013.01); *C08F 2800/20* (2013.01)

(58) Field of Classification Search

None

See application file for complete search history.

(56) References Cited

U.S. PATENT DOCUMENTS

| | | | | |
|---|---|---|---|---|
| 5,103,812 | A * | 4/1992 | Salamone | A61F 13/02 128/DIG. 21 |
| 5,219,560 | A | 6/1993 | Suzuki et al. | |
| 5,409,903 | A * | 4/1995 | Polak | A61K 33/14 514/23 |
| 6,184,407 | B1 | 2/2001 | Yoshitake et al. | |
| 6,280,748 | B1 * | 8/2001 | Morita | C08L 101/005 424/70.121 |
| 6,383,502 | B1 * | 5/2002 | Dunshee | A61Q 3/02 424/59 |
| 6,420,504 | B1 | 7/2002 | Yoshitake et al. | |
| 6,534,590 | B1 | 3/2003 | Aso et al. | |
| 7,488,492 | B2 | 2/2009 | Furukawa et al. | |
| 8,227,086 | B2 * | 7/2012 | Zhao | C08F 220/1808 524/588 |
| 8,410,232 | B2 | 4/2013 | Durant | |
| 9,080,290 | B2 | 7/2015 | Bloembergen et al. | |
| 9,133,309 | B2 | 9/2015 | Iimura et al. | |
| 9,260,607 | B2 | 2/2016 | Iimura et al. | |
| 9,458,346 | B2 | 10/2016 | Overbeek et al. | |
| 9,505,943 | B2 | 11/2016 | Overbeek et al. | |
| 9,593,191 | B2 | 3/2017 | Linemann et al. | |
| 9,649,270 | B2 | 5/2017 | El-Khouri et al. | |
| 9,670,301 | B2 * | 6/2017 | Furukawa | A61Q 19/10 |
| 9,676,889 | B2 | 6/2017 | Nabuurs et al. | |
| 9,932,421 | B2 | 4/2018 | Durant et al. | |
| 10,047,199 | B2 * | 8/2018 | Iimura | A61Q 17/04 |
| 10,172,779 | B2 | 1/2019 | Hori et al. | |

(Continued)

FOREIGN PATENT DOCUMENTS

| | | |
|---|---|---|
| EP | 0976775 | 2/2000 |
| EP | 2513174 | 10/2012 |

(Continued)

OTHER PUBLICATIONS

International Preliminary Report on Patentability for corresponding International Application No. PCT/US2021/053523.
Brandrup, J.; Immergut, E. H.; Grulke, E. A. "Polymer Handbook", 4th edition, page VII/675-714, John Wiley & Sons Inc, 1999.
Fang, "Toward replacement of methyl methacrylate by sustainable bio-based isobornyl methacylate in latex pressure sensitive adhesive", International Journal of Adhesion and Adhesives, 2020, vol. 100, p. 102623.
Grulke, "Solubility Parameter Values", pp. 675-688.

*Primary Examiner* — Sanza L. McClendon

(74) *Attorney, Agent, or Firm* — Catherine U. Brown

(57) ABSTRACT

A silicone-(meth) acrylate copolymer and methods for the preparation and use of the copolymer are provided. The copolymer is soluble in ethanol under ambient conditions. The copolymer, or homogeneous ethanol solution thereof, may be used as a film forming agent in a personal care composition, such as a foundation.

17 Claims, No Drawings

(56) References Cited

U.S. PATENT DOCUMENTS

| | | | | |
|---|---|---|---|---|
| 10,463,737 | B2 | 11/2019 | Huber et al. | |
| 10,808,047 | B2 * | 10/2020 | Gupta | C08F 2/28 |
| 11,180,595 | B2 * | 11/2021 | Souda | C08F 230/08 |
| 2015/0010863 | A1 | 1/2015 | Nabuurs et al. | |
| 2017/0360657 | A1 | 12/2017 | L'Oreal | |
| 2018/0171051 | A1 | 6/2018 | Junk et al. | |
| 2020/0222300 | A1 | 7/2020 | Souda et al. | |

FOREIGN PATENT DOCUMENTS

| | | | | | |
|---|---|---|---|---|---|
| FR | 3064913 | A1 | * | 10/2018 | A61K 8/92 |
| JP | 11001530 | | | 1/1999 | |
| JP | 2000/63225 | | * | 2/2000 | A61K 8/72 |
| JP | 2006052283 | | | 2/2006 | |
| KR | 20170098912 | A | * | 8/2017 | A61K 8/8164 |
| KR | 2018129694 | | | 12/2018 | |
| WO | 9200724 | | | 1/1992 | |
| WO | WO-9200724 | A1 | * | 1/1992 | A61Q 19/00 |
| WO | 0056280 | | | 9/2000 | |
| WO | WO-0056280 | A1 | * | 9/2000 | A61K 47/34 |
| WO | 2012045159 | | | 4/2012 | |
| WO | 2013113938 | | | 8/2013 | |
| WO | 2017108596 | | | 6/2017 | |
| WO | 2018007325 | | | 1/2018 | |
| WO | WO-2019003897 | A1 | * | 1/2019 | C08F 230/08 |
| WO | 2020142370 | | | 7/2020 | |
| WO | 2020142388 | | | 7/2020 | |

* cited by examiner

SILICONE-(METH)ACRYLATE COPOLYMER AND METHODS FOR ITS PREPARATION AND USE IN PERSONAL CARE COMPOSITIONS

CROSS REFERENCE TO RELATED APPLICATIONS

This application is a U.S. national stage filing under 35 U.S.C. § 371 of PCT Application No. PCT/US2021/053523 filed on 5 Oct. 2021, currently pending. which claims the benefit of U.S. Provisional Patent Application No. 63/106,506 filed 28 Oct. 2020 under 35 U.S.C. § 119 (e). PCT Application No. PCT/2021/053523 and U.S. Provisional Patent Application No. 63/106,506 are each hereby incorporated by reference.

TECHNICAL FIELD

This invention relates to a silicone-(meth)acrylate copolymer (copolymer) and methods for the preparation and use of the copolymer. More particularly, the copolymer may be prepared by a free radical polymerization method. The copolymer may be added to personal care compositions suitable for application to the skin. The copolymer may be useful as a film forming agent in personal care compositions.

INTRODUCTION

Film forming agents are important cosmetic raw ingredients, and more often than not, broadly used in personal care compositions, e.g., leave-on products applied to the skin, such as skin care, sunscreen, and color cosmetic products. The DOWSIL™ FA40xx series (where xx=01-04, and 12) offered by Dow Silicones Corporation of Midland, Michigan, USA, have been used as film forming agents in such products. However, there are ongoing needs in the cosmetics industry for sustainable and/or naturally derived ingredients that have one or more of the following properties: water resistance, sebum resistance, rub off resistance, and favorable sensory properties.

SUMMARY

A silicone-(meth)acrylate copolymer and methods for its preparation and use in a personal care composition are provided. This copolymer may be obtained by copolymerizing a mixture of monomers comprising: i) an acrylate monomer, ii) a (meth)acrylate monomer, and iii) an organosiloxane-(meth)acrylate macro-monomer. The copolymer can be used in a personal care composition.

DETAILED DESCRIPTION

The copolymer may be obtained by a method comprising copolymerizing the mixture of monomers described above. More specifically, the mixture of monomers comprises:

15 weight % to 45 weight %, based on combined weights of the monomers, of i) an acrylate monomer of formula

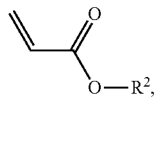

where $R^2$ is a monovalent hydrocarbon group of 1 to 4 carbon atoms;

15 weight % to 40 weight %, based on combined weights of the monomers, of ii) a (meth)acrylate monomer of formula

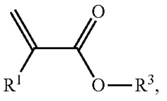

where $R^1$ is selected from the group consisting of hydrogen and methyl, and $R^3$ is a monovalent hydrocarbon group of 8 to 13 carbon atoms; and 20 weight % to 60 weight %, based on combined weights of the monomers, of iii) an organosiloxane-(meth)acrylate macro-monomer of formula $XSi(R^4)_3$, where each X is a (meth)acryloxyalkyl group; each $R^4$ is selected from —$OSi(R^5)_3$ and R, with the proviso that at least two of $R^4$ are —$OSi(R^5)_3$; where each R is a monovalent hydrocarbon group; where each $R^5$ is selected from R, -$DSi(R^6)_3$, and —$[OSiR_2]_m OSiR_3$; where each $R^6$ is selected from R, -$DSi(R^7)_3$, and —$[OSiR2]_m OSiR_3$; where each $R^7$ is selected from R, -$DSi(R^8)_3$, and —$[OSiR2]_m OSiR_3$; where each $R^8$ is selected from R and —$[OSiR_2]_m OSiR_3$; where each D is selected from oxygen and a divalent hydrocarbon group, and where $0 \le m \le 100$. Alternatively, the mixture of monomers may consist essentially of i) the acrylate monomer, ii) the (meth)acrylate monomer and iii) the organosiloxane-(meth)acrylate macro-monomer in the amounts described above. Alternatively, the mixture of monomers may consist of i) the acrylate monomer, ii) the (meth)acrylate monomer and iii) the organosiloxane-(meth) acrylate macro-monomer in the amounts described above. Alternatively, the mixture of monomers may further comprise: iv) up to 20% of an itaconate ester monomer, v) up to 10% of a small methacrylate monomer, or vi) both iv) and v). The combined weight per cents of the monomers in the mixture of monomers total 100%.

i) Acrylate Monomer

Starting material i) is an acrylate monomer of formula:

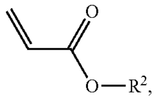

where $R^2$ is a monovalent hydrocarbon group of 1 to 4 carbon atoms. Suitable alkyl groups for $R^2$ include alkyl groups such as methyl, ethyl, propyl (including isopropyl and n-propyl), and butyl (including n-butyl, t-butyl, isobutyl, and sec-butyl). Alternatively, $R^2$ may be an alkyl group of 2 or 3 carbon atoms.

Examples of suitable i) acrylate monomers are known in the art and are commercially available. For example, i) the acrylate monomer may be selected from the group consisting of: methyl acrylate, ethyl acrylate, n-propyl acrylate, isopropyl acrylate, n-butyl acrylate, isobutyl acrylate, tert-butyl acrylate, and a combination of two or more thereof. Alternatively, i) the acrylate monomer may comprise ethyl acrylate. Acrylate monomers are commercially available from various sources, such as Sigma-Aldrich, Inc. of St. Louis, Missouri, USA (Sigma), and The Dow Chemical Company of Midland, Michigan, USA (Dow).

The i) acrylate monomer is used in an amount of 15 weight % to 45 weight %, based on combined weights of the monomers, i.e., combined weights of all the monomers used in the mixture of monomers. Alternatively, the i) acrylate monomer may be used in an amount of at least 15%, alternatively at least 18%, alternatively at least 20%, alternatively at least 25%, and alternatively at least 27%, of the mixture of monomers. At the same time, the i) acrylate monomer may be used in an amount of up to 40%, alternatively up to 33%, alternatively up to 32%, alternatively up to 30%, and alternatively up to 27% of the mixture of monomers.

ii) (Meth)acrylate Monomer

Starting material ii) is a (meth)acrylate monomer of formula

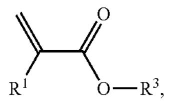

where $R^1$ is selected from the group consisting of hydrogen and methyl, and $R^3$ is a monovalent hydrocarbon group of 8 to 13 carbon atoms. Alternatively, $R^1$ may be methyl. Suitable monovalent hydrocarbon groups for $R^3$ include alkyl groups, which may be linear, branched, cyclic, or combinations thereof. Examples of alkyl groups for $R^3$ include octyl, nonyl, decyl, undecyl, dodecyl (lauryl), tridecyl, and/or branched isomers thereof. Alternatively, the alkyl group may include a cyclic moiety such as an isobornyl group. Alternatively, $R^3$ may be an alkyl group of 10 to 12 carbon atoms or a cycloalkyl group of 10 to 12 carbon atoms. Alternatively, ii) the (meth)acrylate monomer may be selected from the group consisting of tridecyl acrylate, tridecyl methacrylate, lauryl acrylate, lauryl methacrylate, isobornyl acrylate, isobornyl methacrylate, and a combination thereof. Alternatively, ii) the (meth)acrylate monomer may be selected from the group consisting of lauryl acrylate, lauryl methacrylate, isobornyl acrylate, isobornyl methacrylate, and a combination thereof. Alternatively, ii) the (meth)acrylate monomer may be selected from the group consisting of lauryl methacrylate, isobornyl methacrylate, and a combination thereof. The (meth)acrylate monomers described above are commercially available from various sources, such as Fujifilm WAKO Chemicals, Sigma and Dow.

The ii) (meth)acrylate monomer is used in an amount of 15 weight % to 40 weight %, based on combined weights of the monomers. Alternatively, ii) the (meth)acrylate monomer may be used in an amount of at least 15%, alternatively at least 18%, alternatively at least 20%, and alternatively at least 28%, based on combined weights of the monomers. At the same time, the (meth)acrylate monomer may be used in an amount of up to 40%, alternatively up to 35%, alternatively up to 30%, and alternatively up to 28%, on the same basis.

iii) Organosiloxane-(Meth)Acrylate Macro-Monomer

Starting material iii) is organosiloxane-(meth)acrylate macro-monomer (macro-monomer) of formula $XSi(R^4)_3$, where X is a (meth)acryloxyalkyl group; each $R^4$ is selected from $—OSi(R^5)_3$ and R, with the proviso that at least two of $R^4$ are $—OSi(R^5)_3$; where each R is a monovalent hydrocarbon group; where each $R^5$ is selected from R, $-DSi(R^6)_3$, and $—[OSiR_2]_mOSiR_3$; where each $R^6$ is selected from R, $-DSi(R^7)_3$, and $—[OSiR_2]_mOSiR_3$; where each $R^7$ is selected from R, $-DSi(R^8)_3$, and $—[OSiR_2]_mOSiR_3$; where each $R^8$ is selected from R and $—[OSiR_2]_mOSiR_3$; where each D is selected from oxygen and a divalent hydrocarbon group, and where $0 \leq m \leq 100$. Examples of (meth)acryloxyalkyl groups for X include acryloxymethyl, 3-acryloxypropyl, methacryloxymethyl, 3-methacryloxypropyl. Alternatively, X may be 3-methacryloxypropyl. Each R may be an independently alkyl group, as described and exemplified above for $R^2$. Alternatively, each R may be methyl. Each D is independently selected from an oxygen atom and a divalent hydrocarbon group. The divalent hydrocarbon group for D may be an alkylene group of 2 to 10 carbon atoms. Examples include linear alkylene groups such as an ethylene group, a propylene group, a butylene group, and a hexylene group; and branched alkylene groups such as a methyl methylene group, a methyl ethylene group, a 1-methylphenyl group, and a 1,4-dimethyl butylene group. Alternatively, the divalent hydrocarbon group may be ethylene. Alternatively, iii) the macro-monomer may have 4 to 16 silicon atoms, per molecule.

Alternatively, iii) the macro-monomer may have formula:

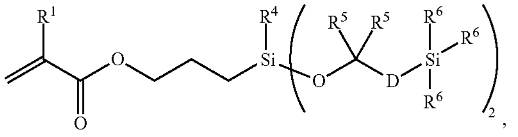

where $R^1$, $R^4$, $R^5$, $R^6$, and D are as described above. Alternatively, the macromonomer may be selected from the group consisting of:

3-(5-((1,1,1,3,5,5,5-heptamethyltrisiloxane-3-yl)oxy)-1,1,1,3,7,9,9,9-octamethyl-3,7-bis((trimethylsilyl)oxy)pentasiloxane-5-yl)propyl methacrylate; 3-(1,5-bis(2-(1,1,1,5,5,5-hexamethyl-3-((trimethylsilyl)oxy)trisiloxane-3-yl)ethyl)-3-(42-(1,1,1,5,5,5-hexamethyl-3-((trimethylsilyl)oxy)trisiloxane-3-yl)ethyl)dimethylsilyl)oxy)-1,1,5,5-tetramethyltrisiloxane-3-yl)propyl methacrylate; and a combination thereof. Suitable macro-monomers are known in the art and may be prepared by known methods, such as those disclosed in Japan Patent Application Publication JP11001530A to Furukawa, et al.; U.S. Pat. No. 6,420,504 to Yoshitake, et al.; and PCT Publication Number WO2020/142388 to Liu, et al.

The iii) macro-monomer is used in an amount of 20 weight % to 60 weight % based on combined weights of the monomers. Alternatively, the amount of iii) the macro-monomer may be at least 20%, alternatively at least 25%, alternatively at least 30%, and alternatively at least 35%, based on combined weights of the monomers. At the same time, the amount of iii) the macro-monomer may be up to 60%, alternatively up to 50%, alternatively up to 45%, alternatively up to 42%, alternatively up to 40%, and alternatively up to 35%, on the same basis.

iv) Itaconate Ester Monomer

Starting material iv) is an itaconate ester monomer that may optionally be added to the mixture of monomers used to prepare the copolymer. The iv) itaconate ester monomer has formula

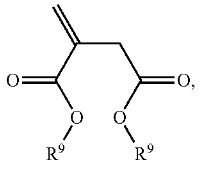

where each $R^9$ is an independently selected alkyl group of 1 to 8 carbon atoms. The alkyl group is exemplified by linear, branched, and/or cyclic alkyl groups such as methyl, ethyl, propyl (including isopropyl and n-propyl), butyl (including n-butyl, t-butyl, isobutyl, and sec-butyl); and linear pentyl, hexyl, heptyl and octyl groups (as well as branched alkyl groups of 5-8 carbon atoms; and cyclopentyl, cyclohexyl and/or cyclooctyl. Alternatively, each $R^9$ may be methyl, ethyl, propyl or butyl; alternatively, each $R^9$ may be methyl or butyl. Examples of suitable iv) itaconate ester monomers include dimethyl itaconate and dibutyl itaconate. Itaconate ester monomers are known in the art and are commercially available, e.g., from Sigma.

The iv) itaconate ester monomer can be used in an amount up to 20 weight %, alternatively >0 to 20 weight %, based on combined weights of the monomers. When present, the iv) itaconate ester monomer may be present in an amount of >0%, alternatively at least 5%, alternatively at least 7%, and alternatively at least 10%, based on combined weights of the monomers. At the same time, the iv) itaconate ester monomer may be present in an amount up to 20%, alternatively up to 17%, and alternatively up to 15%, on the same basis.

v) Small Methacrylate Monomer

Starting material v) is an additional methacrylate monomer that differs from i) and ii) described above, and which may optionally be added to the mixture of monomers used to prepare the copolymer described above. The v) additional methacrylate monomer has formula

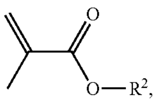

where $R^2$ is as described above. Examples of suitable v) additional methacrylate monomers include methyl methacrylate, ethyl methacrylate, n-propyl methacrylate, isopropyl methacrylate, n-butyl methacrylate, isobutyl methacrylate, tert-butyl methacrylate, or a combination of two or more thereof. The v) small methacrylate monomers are commercially available from various sources, such as Sigma and Dow.

When present, the v) additional methacrylate monomer may be present in an amount of >0%, alternatively at least 1%, alternatively at least 2%, alternatively at least 3%, alternatively at least 4%, and alternatively at least 5%, based on combined weights of the monomers. At the same time, the v) additional methacrylate monomer may be present in an amount up to 10%, alternatively up to 9%, alternatively up to 8%, alternatively up to 7%, and alternatively up to 6%, on the same basis. When v) the additional methacrylate monomer is present, the amount of i) the acrylate monomer may be toward the lower end of the range described above, e.g., 15% to <30%.

Method for Preparing the Copolymer

The copolymer may be prepared by a method comprising: 1) copolymerizing the mixture of monomers in the presence of a radical initiator, and optionally a solvent; thereby forming a reaction mixture; and 2) quenching the reaction mixture. The method may optionally further comprise 3) purifying the copolymer, and/or 4) dissolving the copolymer in a simple alcohol such as ethanol.

In step 1), the mixture of monomers may be copolymerized by mixing and heating to form a reaction mixture. The copolymerization may be performed by a radical polymerization, and a radical initiator may be combined with the mixture of monomers in step 1).

The radical initiator may be, for example, an azobis-based compound, an organic peroxide, and a combination thereof. The radical initiator may comprise, for example, an azobis-based compound such as 2,2'-azobis(isobutyronitrile); 2,2'-azobis(2-methyl)butyronitrile; 2,2'-azobis(2,4-dimethylvaleronitrile); dimethyl-2,2'-azobis(2-methyl propionate); and a combination of two or more thereof. Alternatively, the radical initiator may comprise, for example, an organic peroxide such as benzoyl peroxide, lauroyl peroxide, tert-butyl peroxybenzoate; tert-butyl peroxy-2-ethylhexanoate, tert-amyl peroxypivalate, cyclohexanone peroxide, isopropyl cumyl hydroperoxide, di-tert-butyl peroxide, diisopropyl percarbonate, tert-butyl perbenzoate, tert-butyl peroctanoate, bis(3,5,5-trimethyl)hexanoyl peroxide, tert-butylperoxypivalate, and combinations of two or more thereof. The radical initiators are known in the art and are commercially available. For example, organic peroxides such as peroxydicarbonates, diacylperoxides, dialkyl peroxides, and peroxyeters are available under the tradename LUPEROX™ from Arkema Inc. of King of Prussia, Pennsylvania, USA. The amount of radical initiator may be 0.1 weight parts to 5 weight parts, per 100 parts by weight of the mixture of monomers used in step 1).

The copolymerization may be a solution polymerization, and a solvent may be added in step 1). One or more of the starting materials (e.g., the radical initiator and/or iii) the macro-monomer) may be delivered in a solvent. For example, the radical initiator may be delivered in mineral spirits. The solvent for solution polymerization may be in addition to, or instead of, the solvent for delivery of a starting material. The solvent in step 1) may comprise a simple alcohol of formula $R^2OH$, where $R^2$ is as described above. The simple alcohol is exemplified by ethanol, n-propanol, isopropanol, n-butanol, t-butanol, or a combination thereof. The simple alcohol may comprise ethanol. Alternatively, the simple alcohol may be selected from ethanol, isopropanol, or a combination thereof.

Step 1) may be performed for example in a batch, semi-batch, or continuous mode over 3 hours to 20 hours at a temperature from >30° C., alternatively 50° C. to 150° C. In the semi-batch mode, a fraction of the reagents may be dosed into the reactor (e.g., the radical initiator, the mixture of monomers, and/or the solvent in which the radical initiator and the mixture of monomers is delivered), and the rest of the reagents are metered into the reactor over a targeted feed time, typically 1 hour to 20 hours. In the continuous mode, the reagents are continuously metered into the reactor, and the reaction mixture comprising the copolymer is continuously withdrawn from the reactor. The starting materials used in step 1) may be free of acids.

In step 2), quenching may be performed by cooling the reaction mixture to 25±5° C.

The method may optionally further comprise step 3) purification of the copolymer. Purification can be carried out by any convenient means. For example, if any unreacted monomer or monomers are present, and/or solvents are used, these may be removed, e.g., by heating, optionally with reduced pressure. For example, stripping and/or distillation may be used to purify the copolymer. Alternatively, the unreacted monomers may be reduced by chemical chase, in which an additional radical initiator is added to consume the unreacted monomers and bring the level down to sufficiently low level (e.g., <500 ppm) that the unreacted monomers do not need to be removed.

The method may optionally further comprise step 4) dilution of the copolymer with a simple alcohol comprising ethanol. Without wishing to be bound by theory, it is thought that for ease of blending the copolymer into a personal care composition and/or stability of the resulting personal care composition, a homogenous solution of the copolymer in ethanol may be desired. The homogeneous solution may comprise 10 weight % to 90 weight % ethanol and 10 weight % to 90 weight % copolymer (alternatively 40% to 60% copolymer with the balance being ethanol). For example, a personal care composition such as a cosmetic suitable for application to skin (e.g., a foundation) may be formulated including the copolymer described herein. Without wishing to be bound by theory, it is thought that an oil (such as a silicone oil) is not necessary for delivery of the copolymer described herein. Furthermore, because a homogeneous solution of the copolymer dissolved in ethanol may be provided which is stable (does not phase separate) at room temperature (25±5° C.) for at least 6 months, it is thought that the copolymer described herein can provide improved stability over previously proposed silicone-(meth)acrylate copolymers.

Alternatively, the method may further comprise a solvent exchange step 5) after step 3) or after step 4). If a different carrier for the copolymer is desired, the simple alcohol described above may be removed and replaced with the different carrier. Any desired carrier with a solubility parameter of 14.0-28.0 MPa1/2 may be used, where the solubility parameter is as described in Brandrup, J.; Immergut, E. H.; Grulke, E. A. "Polymer Handbook", 4th edition, page VII/675-714, John Wiley & Sons Inc, 1999. ISBN: 0-471-16628-6. Alternatively, the carrier may be selected from the group consisting of alternative alcohols including monohydric alcohols such as isopropyl alcohol, n-propanol, tert-butanol, and sec-butanol, polyhydric alcohols including dihydric alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, and octylene glycol, trihydric alcohols such as trimethylolpropane, and 1,2,6-hexanetriol, tetrahydric alcohols and higher such as pentaerythritol and xylitol, sugar alcohols such as sorbitol, ketones including acetone and methyl ethyl ketone, fatty acid esters including isopropyl myristate and isopropyl palmitate, natural oils including sunflower seed oil, caprylic/capric triglycerides, coconut oil, castor oil, argan oil, and jojoba oil, hydrocarbon oils including isododecane, isohexadecane, paraffin, isoparaffin, squalane, and squalene, and an alkane of 9 to 11 carbon atoms, siloxane or silicone oils such as decamethylcyclopentyasiloxane (D5) and linear low-viscosity polydimethylsiloxane (PDMS), glycerin; or a combination of two or more thereof.

Copolymer

The copolymer prepared as described herein may have a number average molecular weight (Mn) of 2 to 100 kg/mol, alternatively 5 to 50 kg/mol, and alternatively 10.1 to 10.9 kg/mol The copolymer may have a weight average molecular weight (Mw) of 5 to 1000 kg/mol, alternatively 20 to 200 kg/mol, and alternatively 23.0 to 29.0 kg/mol. The copolymer may have a polydispersity of 2 to 10, alternatively 2 to 5, and alternatively 2.25 to 2.89. Mn and Mw may be measured by gel permeation chromatography with tetrahydrofuran that contained 1 weight % formic acid as the mobile phase relative to polystyrene standards, and polydispersity may be calculated from Mn and Mw measured as described above.

The silicone-(meth)acrylate copolymer prepared as described herein may have up to 60% of the copolymer backbone made up of carbon atoms. Alternatively, when the copolymer is delivered in solution, the solution may have up to 84% carbon content based on weight of the solution. It is desirable that the carbon content of the copolymer, and solution thereof, is derived from renewable resources other than fossil fuels or natural gas. When used in a personal care composition for application to the skin, the copolymer described herein may provide the benefit of good water resistance (as shown by water contact angles) good sebum resistance, and/or good rub-off resistance, as described in the examples below.

Personal Care Composition

The copolymer prepared as described herein may be added into a personal care composition. For example, the copolymer described above may act as a film forming agent in a personal care composition. The personal care composition is not specifically restricted, however, the personal care composition may be a leave-on product suitable for application to the skin, such as skin care, sunscreen, and color cosmetic products (e.g., a foundation) The copolymer, or solution of copolymer, prepared as described above may be added to the personal care composition by any convenient means, such as mixing. The personal care composition may comprise the copolymer described above in any amount, e.g., at least 1%, alternatively at least 2%, alternatively at least 5%, alternatively at least 10%, alternatively at least 20%, and alternatively at least 30%, based on weight of all components of the personal care composition (and excluding the carrier for delivery of the copolymer). At the same time, the personal care composition may comprise the copolymer described above in an amount of up to 99%, alternatively up to 90%, alternatively up to 80%, alternatively up to 70%, alternatively up to 50%, alternatively up to 10%, alternatively up to 8%, and alternatively up to 6%, based on weight of all components of the personal care composition (and excluding the carrier for delivery of the copolymer). The exact amount of copolymer used depends on various factors, such as the type of personal care composition to be formulated. Alternatively, the personal care composition may contain the copolymer in an amount of 1 weight % to 99 weight %, alternatively 5% to 95%, alternatively 1% to 10%, alternatively 2% to 8%, and alternatively 4% to 6%, based on weight of all components of the personal care composition (and excluding the carrier for delivery of the copolymer). The copolymer prepared as described above, may be used in place of the different copolymers in personal care compositions known in the art, such as those disclosed in U.S. Pat. No. 6,280,748 to Morita, et al.; U.S. Pat. No. 7,488,492 to Furukawa, et al.; U.S. Pat. No. 9,670,301 to Furukawa, et al.; U.S. Pat. No. 10,047,199 to Iimura, et al.; U.S. Pat. No. 10,172,779 to Hori, et al.; and U.S. Patent Application Publication 2020/0222300 to Souda, et al.

EXAMPLES

The following examples are provided to illustrate the invention to one skilled in the art and are not to be construed as limiting the scope of the invention set forth in the claims. Starting materials used in these examples are described in Table 1.

TABLE 1

| Starting Materials | | | |
|---|---|---|---|
| Monomer | Abbreviation | Chemical Name | Source |
| i) | EA | Ethyl acrylate | Dow |
| i) | BA | n-Butyl acrylate | Dow |
| v) | MMA | methyl methacrylate | Dow |
| ii) | IBOMA | Isobornyl methacrylate | Sigma |
| ii) | LMA | Lauryl methacrylate | Sigma |
| comparative | SMA | Stearyl methacrylate | TCI America |
| ii) | LA | Lauryl acrylate | TCI America |
| ii) | C13MA | Methacrylic ester 13.0 CAS #90551-76-1 | Evonik |
| iii) | Si16PrMA | 3-(1,5-bis(2-(1,1,1,5,5,5-hexamethyl-3-((trimethylsilyl)oxy)trisiloxan-3-yl)ethyl)-3-(((2-(1,1,1,5,5,5-hexamethyl-3-((trimethylsilyl)oxy)trisiloxan-3-yl)ethyl)dimethylsilyl)oxy)-1,1,5,5-tetramethyltrisiloxan-3-yl)propyl methacrylate | Dow Silicones Corporation |
| iii) | Si10PrMA | 3-(5-((1,1,1,3,5,5,5-heptamethyltrisiloxan-3-yl)oxy)-1,1,1,3,7,9,9,9-octamethyl-3,7-bis((trimethylsilyl)oxy)pentasiloxan-5-yl)propyl methacrylate | Synthesized as described in PCT Publication WO2020/142370 to Liu, et al. |
| iv) | DBI | Di(n-butyl) itaconate | Sigma |
| | EtOH | Ethanol | Greenfield Global |
| | ACT 96-TRI-77891 | surface-treated titanium dioxide | Miyoshi America, Inc. |
| | ACT96-Y-77492 | surface-treated yellow iron oxide | Miyoshi America, Inc. |
| | ACT96-B-77499 | surface-treated black iron oxide | Miyoshi America, Inc. |
| | ACT96-R-77491 | used in Table 3 | Miyoshi America, Inc. |
| | IDD | Isododecane | Makingcosmetics.com |
| | DOWSIL™ ES-5300 Formulation Aid | silicone emulsifier/formulation aid, INCI: Lauryl PEG-10 Tris(Trimethylsiloxy)silylethyl Dimethicone | Dow Silicones Corporation |
| | DOWSIL™ FZ-3196 | Caprylyl Methicone. Carrier. | Dow Silicones Corporation |
| | NaCl | Sodium chloride | Sigma |
| | | Glycerine | Makingcosmetics.com |
| | Euxyl PE9010 | Liquid cosmetic preservative, INCI: Phenoxyethanol (and) Ethylhexylglycerin | Schülke Inc. |
| | IPA | Isopropyl alcohol | Dow |

In this Reference Example 1, samples of copolymers were prepared according to the following general procedure. A 300-mL, straight-wall glass resin reactor was equipped with a 4-pitched stainless steel propeller, a water condenser, and a thermocouple, and housed in a 4-well, temperature-controlled block (PolyBLOCK, Parallel Synthesis) designed by HEL Group (www.helgroup.com). The propeller was driven by an overhead mechanical stirrer, and the thermocouple was connected with a J-KEM temperature controller and provided input to the PolyBLOCK unit to achieve the desired temperature. The flask was first charged with 50.0 g of ethanol (SDA 3-C grade, a mixture of 200-proof ethanol and isopropanol at a ratio of 95.24:4.76 by volume) and the temperature was allowed to raise to 78° C. A $N_2$ blanket was applied to remove the entrained air, and the agitation rate was at 300 rpm to allow adequate stirring (indicated by a small vortex at the center). In a separate 1-L glass jar, monomers were combined and allowed to form a homogeneous mixture with the aid of magnetic stirring. Selections and amounts of each monomer are shown in Table 2, below. The co-fed initiator was 1.71 g of Trigonox 125-C75 (tert-amyl peroxypivalate, 75% active in mineral spirits) in 43.49 g of SDA 3-C ethanol.

When the temperature of the reactor reached 78° C., 5.0 g of the monomer mixture was fed into the reactor and heat continued to be applied. The rest of the monomer mixture and the co-feed initiator started to be metered in at the rate of 0.63 g/min and 0.30 g/min, respectively, over 150 min. Moderate reflux was observed throughout the polymerization. When the monomer mixture feed was completed, 11.84 g of SDA 3-C ethanol was added into the monomer jar and rinsed into the reactor. The batch was held at 78° C. for 15 min. Then two chemical chases of 2.54 g of Trigonox 125-C75 in 8.57 g of SDA 3-C ethanol were metered in at a rate of 0.37 g/min over 30 min with a 15-min hold in between. Then the batch was held for another 15 min before being quenched by air cooling. 66.35 g of SDA 3-C grade ethanol was added during cooling as the final dilution. The resulting copolymer solutions were then analyzed as follows.

Turbidity Measurement

The turbidity of the copolymer solutions were measured by referring to the ASTM D7315-17 method, "Standard Test Method for Determination of Turbidity Above 1 Turbidity Unit (TU) in Static Mode". ASTM D7315-17 applies for the turbidity in water, but the same principle applies, and the method was used for these solution polymers in various organic solvents such as ethanol without modification. A 1-oz clear, glass vial was filled with a copolymer solution at 23° C. Caution was taken to minimize disturbance of the copolymer solution to avoid air entrainment. The turbidity was measured in a Micro 100 turbidimeter from HF Scientific, Inc. The turbidimeter was freshly calibrated with a ProCal Calibration kit (which comprises three standards of 1000 NTU, 10 NTU, and 0.02 NTU) from HF Scientific, Inc. The turbidity was reported in nephelometric turbidity unit (NTU).

Foundation Formulation

Foundation formulation samples were prepared by combining the ingredients in the amounts shown in Table 3, as follows. Mix the ingredients of Phase B together with an overhead mixer at a speed of <500 rpm. Mix the ingredients of Phase A together with Flacktek equipment. Add Phase A to B. Mix the ingredients of Phase C together. Add Phase C slowly to the mixture of Phases A and B (drops) while high mixing (over 1200 rpm) with the overhead mixer. Check pH, viscosity and make observations the next day.

Contact Angle Measurement of Polymer and Foundation Films

Contact angle data were acquired from the surface of each film using both water and sebum on a Kruss DSA100 instrument. Data were acquired as quickly as possible (0 seconds) and after approximately 200 seconds on the same drop. There were two types of films from which contact angles were measured, i.e., —neat polymer films (from a copolymer solution in ethanol directly cast) or foundation films (from a foundation formulation containing a copolymer and cast into a film. Data from Table 2 show the neat copolymer films, and data from Table 4 are from foundation films). Thin films of the copolymers or foundation formulations were prepared on an automated high-throughput coating station or manually using a 6 mil doctor blade on LENETA P121-16 black plastic charts. The films were dried in an environmental controlled room (22° C., 50% relative humidity) for at least 72 hours. Tables 2 and 4 list contact angle measurements from these two types of films.

Sebum Resistance

The sebum contact angles were measured and used to gauge the sebum resistance of the neat polymers and foundation formulations. Contact angle data were acquired from the surface of each film using both water and sebum on a Kruss DSA100 instrument. Data were acquired as quickly as possible (0 seconds) and after approximately 200 seconds on the same drop. The higher numbers are associated with higher resistance and vice versa.

Glass Transition Temperature

A small amount of copolymer solution was transferred to an aluminum pan, first dried at ambient temperature, and then at 60° C. under house vacuum for at least 24 hours until constant mass was achieved. The dried copolymer mass was typically 3 to 10 mg. The aluminum pan was hermetically sealed and analyzed on a Q1000 differential scanning calorimeter from TA Instruments. Two heating scans were applied between −90° C. and 150° C. at a rate of 20° C./min. Tg was taken as the middle point during the step change of the heat flow, and the measurement from the second heating scan of each sample was reported.

TABLE 2

Composition, Solubility in Ethanol, Turbidity, Water Contact Angle and Sebum Resistance of the Copolymer Samples prepared according to the procedure in Reference Example 1

| Examples | Amount in weight parts and Monomers in the Monomer Mixture used to Prepare the Copolymer | Copolymer Soluble in ethanol? | Turbidity (NTU) | $T_g$ by DSC (° C.) | CA water t = 0 s (°) average | CA sebum t = 0 s (°) average | CA water t = 250 s (°) average | CA sebum t = 250 s (°) average |
|---|---|---|---|---|---|---|---|---|
| Comparative example 1 | 20 LMA/30 IBOMA/50 Si16PrMA | N | NM | NM | NM | NM | NM | NM |
| Comparative example 2 | 20 LMA/10 IBOMA/40 DBI/30 Si16PrMA | N | >1000 | NM | NM | NM | NM | NM |
| Comparative example 3 | 5 EA/20 LMA/10 IBOMA/35 DBI/30 Si16PrMA | N | >1000 | NM | NM | NM | NM | NM |
| Comparative example 4 | 33 EA/5 LMA/42 IBOMA/20 Si16PrMA | N | NM | NM | NM | NM | NM | NM |
| Comparative example 5 | 26 EA/10 LMA/44 IBOMA/20 Si16PrMA | N | NM | NM | NM | NM | NM | NM |
| Comparative example 6 | 8 BA/27 MMA/20 SMA/45 Si16PrMA | N | >1000 | NM | NM | NM | NM | NM |
| Comparative example 7 | 30 MMA/20 LA/50 Si16PrMA* | Y | 5.20 | NM | NM | NM | NM | NM |
| Comparative example 8 | 12 BA/38 MMA/50 Si16PrMA | Y | 0.70 | 27.7 | 100.6 | 50.1 | 96.5 | 49.5 |
| Comparative example 9 | 12 BA/38 MMA/50 Si16PrMA | Y | 2.92 | 8.5 | 99.0 | 60.5 | 96.7 | 59.4 |
| Comparative example 10 | 12 BA/38 MMA/50 Si16PrMA | Y | 0.60 | 0.4 | 101.0 | 57.4 | 97.0 | 56.2 |
| Inventive example 1 | 33 EA/20 LMA/10 IBOMA/7 DBI/30 Si16PrMA | Y | NM | −30.1 | 112.1 | 67.5 | 75.4 | 31.9 |
| Inventive example 2 | 33 EA/30 IBOMA/7 DBI/30 Si16PrMA | Y | 3.23 | 2.3 | 101.1 | 40.3 | 100.0 | 35.1 |
| Inventive example 3 | 40 EA/20 LMA/10 IBOMA/30 Si16PrMA | Y | NM | −30.1 | 111.1 | 70.3 | 70.0 | 27.7 |
| Inventive example 4 | 40 EA/30 IBOMA/30 Si16PrMA | Y | 1.23 | −0.2 | 100.9 | 37.8 | 98.2 | 34.6 |
| Inventive example 5 | 40 EA/40 IBOMA/20 Si16PrMA | Y | 7.65 | 10.5 | 98.2 | 41.9 | 96.2 | 29.9 |
| Inventive example 6 | 18 EA/35 IBOMA/17 DBI/30 Si16PrMA | Y | 4.76 | NM | 98.8 | 37.5 | 96.8 | 29.8 |
| Inventive example 7 | 30 EA/30 IBOMA/20 DBI/20 Si16PrMA | Y | 1.50 | 7.5 | 99.3 | 38.9 | 98.0 | 34.8 |
| Inventive example 8 | 20 EA/30 IBOMA/20 DBI/30 Si16PrMA | Y | 1.92 | 6.6 | 99.0 | 37.2 | 97.1 | 34.1 |
| Inventive example 9 | 30 EA/30 IBOMA/10 DBI/30 Si16PrMA | Y | 2.02 | 8.0 | 100.9 | 37.8 | 98.6 | 33.6 |
| Inventive example 10 | 30 EA/30 IBOMA/5 DBI/35 Si16PrMA | Y | 2.91 | 5.2 | 101.7 | 34.9 | 99.1 | 32.4 |

TABLE 2-continued

Composition, Solubility in Ethanol, Turbidity, Water Contact Angle and Sebum Resistance of the Copolymer Samples prepared according to the procedure in Reference Example 1

| Examples | Amount in weight parts and Monomers in the Monomer Mixture used to Prepare the Copolymer | Copolymer Soluble in ethanol? | Turbidity (NTU) | $T_g$ by DSC (° C.) | CA water t = 0 s (°) average | CA sebum t = 0 s (°) average | CA water t = 250 s (°) average | CA sebum t = 250 s (°) average |
|---|---|---|---|---|---|---|---|---|
| Inventive example 11 | 32 EA/28 IBOMA/40 Si16PrMA | Y | 2.20 | 3.2 | 103.3 | 37.3 | 100.8 | 35.4 |
| Inventive example 12 | 27 EA/18 IBOMA/10 MMA/45 Si16PrMA | Y | 1.31 | −0.3 | 106.4 | 38.8 | 104.9 | 32.0 |
| Inventive example 13 | 25 EA/15 IBOMA/10 MMA/50 Si16PrMA | Y | 1.55 | −4.4 | 110.8 | 43.4 | 107.2 | 31.9 |
| Inventive example 14 | 40 EA/20 LMA/10 IBOMA/30 Si16PrMA | Y | 1.32 | −30.6 | 111.5 | 74.5 | 70.9 | 30.3 |
| Inventive example 15 | 25 EA/35 IBOMA/15 DBI/25 Si16PrMA | Y | NM | 10.6 | 98.1 | 38.1 | 96.4 | 30.1 |
| Inventive example 16 | 30 EA/30 IBOMA/10 DBI/30 Si10PrMA | Y | 2.27 | 4.6 | 98.4 | 39.4 | 96.6 | 35.2 |
| Inventive example 17 | 32 EA/28 IBOMA/40 Si10PrMA | Y | 2.63 | −0.5 | 103.9 | 40.1 | 100.3 | 37.7 |
| Inventive example 18 | 25 EA/15 IBOMA/10 MMA/50 Si10PrMA | Y | 2.26 | −6.1 | 104.8 | 44.5 | 102.6 | 39.3 |
| Inventive example 19 | 30 EA/28 IBOMA/42 Si16PrMA | Y | 2.52 | NM | NM | NM | NM | NM |
| Inventive example 20 | 32 EA/28 IBOMA/40 Si16PrMA | Y | 2.37 | NM | NM | NM | NM | NM |
| Inventive example 21 | 40 EA/20 C13MA/10 IBOMA/30 Si16PrMA | Y | 1.89 | NM | NM | NM | NM | NM |

In the table above, NM means not measured.

Comparative examples 1 and 2 have no monomer corresponding to i). Comparative example 3 contains an amount of i) EA that is too low (<15%) and an amount of iv) DBI that is too high (>20%). Comparative example 4 is contains an amount of a ii) combination of LMA and IBOMA (5+42=47%) that is too high (>40%). Comparative example 5 contains an amount of a ii) combination of LMA and IBOMA (10+44=54%) that is too high (>40%). Comparative example 6 is comparative because SMA has too many carbon atoms. Comparative examples 1 to 6 show that when the amounts of each monomer differ from those in this invention, the resulting copolymer is not sufficiently soluble in the simple alcohol (ethanol) for the present application. Comparative example 7 is a repeat of comparative example 3 of US2020/0222300 and does not contain i) an acrylate monomer. The * denotes that the monomer mixture of comparative example 7 did not react completely; it had conversion of only 95%, resulting in unreacted silicone-(meth)acrylate macro-monomer, which is the most expensive component of the copolymer.

The Inventive Examples showed that when the mixture of monomers (selection and amount of each monomer) is used as described herein, the monomers reacted completely (high conversion of ≥99%); the resulting copolymer is soluble in ethanol and has glass transition temperature, water resistance and/or sebum resistance suitable for personal care applications. The combination of these monomers showed great reaction kinetics using free-radical polymerization, as exemplified by the solution polymerization with high conversion. Furthermore, the polymerization can be directly carried out in ethanol, one commercially ubiquitous carrier sourced from biomass. No solvent exchange is required to remove excess residual monomers to meet requirements for personal care applications, reducing the production cost and streamlining the supply chain. Furthermore, the inventors found that the copolymers of the present invention had the following benefits:

1. In-foundation performance of inventive examples have demonstrated superior water repellency, and
2. In-foundation performance of inventive examples have demonstrated durable sebum repellency (demonstrated by significantly higher CA sebum 250s values over comparatives).

TABLE 3

Foundation formulation

| | A w/w % | B w/w % | C w/w % | D w/w % | E w/w % | F w/w % | G w/w % |
|---|---|---|---|---|---|---|---|
| Phase A | | | | | | | |
| ACT 96-TRI-77891 | 5.81 | 5.81 | 5.81 | 5.81 | 5.81 | 5.81 | 5.81 |
| ACT96-Y-77492 | 1.09 | 1.09 | 1.09 | 1.09 | 1.09 | 1.09 | 1.09 |
| ACT96-B-77499 | 0.07 | 0.07 | 0.07 | 0.07 | 0.07 | 0.07 | 0.07 |
| ACT96-R-77491 | 0.25 | 0.25 | 0.25 | 0.25 | 0.25 | 0.25 | 0.25 |
| IDD | 12.00 | 12.00 | 12.00 | 12.00 | 12.00 | 12.00 | 12.00 |
| Phase B | | | | | | | |
| DOWSIL ™ ES-5300 Formulation Aid | 6.00 | 6.00 | 6.00 | 6.00 | 6.00 | 6.00 | 6.00 |
| DOWSIL ™ FZ-3196 | 3.28 | 3.28 | 3.28 | 3.28 | 3.28 | 3.28 | 3.28 |

TABLE 3-continued

| Foundation formulation | | | | | | | |
|---|---|---|---|---|---|---|---|
| Copolymer of Comparative Example 8 | 12.50 | 0 | 0 | 0 | 0 | 0 | 0 |
| Copolymer of Inventive Example 6 | 0 | 11.70 | 0 | 0 | 0 | 0 | 0 |
| Copolymer of Inventive Example 15 | 0 | 0 | 11.90 | 0 | 0 | 0 | 0 |
| copolymer of Inventive Example 2 | 0 | 0 | 0 | 11.85 | 0 | 0 | 0 |
| copolymer of Inventive Example 4 | 0 | 0 | 0 | 0 | 11.16 | 0 | 0 |
| copolymer of Inventive Example 7 | 0 | 0 | 0 | 0 | 0 | 12.05 | 0 |
| Copolymer of Comparative Example 9 | 0 | 0 | 0 | 0 | 0 | 0 | 11.85 |
| Phase C | | | | | | | |
| Water | 52.00 | 52.80 | 52.60 | 53.34 | 52.45 | 52.65 | 52.65 |
| Sodium Chloride | 1.00 | 1.00 | 1.00 | 1.00 | 1.00 | 1.00 | 1.00 |
| Glycerin | 5.00 | 5.00 | 5.00 | 5.00 | 5.00 | 5.00 | 5.00 |
| Euxyl PE9010 | 1.00 | 1.00 | 1.00 | 1.00 | 1.00 | 1.00 | 1.00 |
| Total | 100.00 | 100.00 | 100.00 | 100.69 | 99.11 | 100.20 | 100.00 |

| | H w/w % | I w/w % | J w/w % | K w/w % | L w/w % | M w/w % | N w/w % |
|---|---|---|---|---|---|---|---|
| Phase A | | | | | | | |
| ACT 96-TRI-77891 | 5.81 | 5.81 | 5.81 | 5.81 | 5.81 | 5.81 | 5.81 |
| ACT96-Y-77492 | 1.09 | 1.09 | 1.09 | 1.09 | 1.09 | 1.09 | 1.09 |
| ACT96-B-77499 | 0.07 | 0.07 | 0.07 | 0.07 | 0.07 | 0.07 | 0.07 |
| ACT96-R-77491 | 0.25 | 0.25 | 0.25 | 0.25 | 0.25 | 0.25 | 0.25 |
| IDD | 12.00 | 12.00 | 12.00 | 12.00 | 12.00 | 12.00 | 12.00 |
| Phase B | | | | | | | |
| DOWSIL ™ ES-5300 Formulation Aid | 6.00 | 6.00 | 6.00 | 6.00 | 6.00 | 6.00 | 6.00 |
| DOWSIL ™ FZ-3196 | 3.28 | 3.28 | 3.28 | 3.28 | 3.28 | 3.28 | 3.28 |
| Copolymer of Inventive Example 10 | 11.68 | 0 | 0 | 0 | 0 | 0 | 0 |
| Copolymer of Inventive Example 11 | 0 | 11.79 | 0 | 0 | 0 | 0 | 0 |
| Copolymer of Inventive Example 12 | 0 | 0 | 11.55 | 0 | 0 | 0 | 0 |
| Copolymer of Inventive Example 13 | 0 | 0 | 0 | 12.11 | 0 | 0 | 0 |
| Copolymer of Inventive Example 16 | 0 | 0 | 0 | 0 | 11.03 | 0 | 0 |
| Copolymer of Inventive Example 17 | 0 | 0 | 0 | 0 | 0 | 12.11 | 0 |
| Copolymer of Inventive Example 18 | 0 | 0 | 0 | 0 | 0 | 0 | 11.52 |
| Phase C | | | | | | | |
| Water | 52.82 | 52.71 | 52.95 | 52.39 | 53.47 | 52.39 | 52.98 |
| Sodium Chloride | 1.00 | 1.00 | 1.00 | 1.00 | 1.00 | 1.00 | 1.00 |
| Glycerin | 5.00 | 5.00 | 5.00 | 5.00 | 5.00 | 5.00 | 5.00 |
| Euxyl PE9010 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 |

Amounts of each copolymer are shown as the amount of solution (wt %) added. The target was to provide 5% of the copolymer (excluding carrier) in the foundation formulation.

TABLE 4

Contact angle performance of copolymers in the foundation formulation

| Foundation Formulation # | Copolymer | Carrier | CA water 0 s | CA water 0 s stdev | CA sebum 0 s | CA sebum 0 s stdev | CA water 250 s | CA water 250 s stdev | CA sebum250s | CA sebum 250 s stdev |
|---|---|---|---|---|---|---|---|---|---|---|
| Formulation A in Table 3 | Comparative example 8 | IDD | 101.7 | 0.9 | 52.5 | 1.1 | 98 | 2.7 | 18.1 | 1 |
| Formulation G | Comparative example 9 | EtOH | 114.5 | 1.3 | 49.8 | 1.3 | 109.8 | 1.1 | 18.5 | 0.4 |
| Formulation O | Comparative example 10 | IPA | 112.5 | 0.9 | 51.6 | 4.2 | 107.3 | 0.7 | 18.9 | 1 |
| Formulation D | Inventive example 2 | EtOH | 123.7 | 1 | 51.9 | 4.5 | 111.4 | 2.1 | 28.4 | 0.9 |
| Formulation E | Inventive example 4 | EtOH | 124.7 | 1 | 43.5 | 0.8 | 116.7 | 1.5 | 26.9 | 0.7 |
| Formulation B | Inventive example 6 | EtOH | 128.7 | 0.9 | 39 | 0.7 | 122.7 | 2.3 | 23.6 | 0.5 |
| Formulation F | Inventive example 7 | EtOH | 128.5 | 0.9 | 41 | 0.5 | 118.5 | 2 | 25.5 | 1.4 |
| Formulation H | Inventive example 10 | EtOH | 128.3 | 0.9 | 44.1 | 0.4 | 117.6 | 2.2 | 26.8 | 1.2 |
| Formulation I | Inventive example 11 | EtOH | 126.5 | 1.1 | 43.2 | 0.4 | 113.5 | 0.7 | 28.4 | 1.4 |
| Formulation J | Inventive example 12 | EtOH | 130.2 | 1.7 | 41.5 | 1 | 118.9 | 1.1 | 25.8 | 1.1 |
| Formulation K | Inventive example 13 | EtOH | 128.3 | 1.3 | 42.1 | 0.5 | 119.7 | 3.3 | 24.8 | 1.1 |
| Formulation L | Inventive example 16 | EtOH | 127 | 1.1 | 41.7 | 0.4 | 118.4 | 1.1 | 25 | 0.6 |
| Formulation M | Inventive example 17 | EtOH | 125 | 1.1 | 41.7 | 2 | 112 | 1 | 24.4 | 1.6 |
| Formulation N | Inventive example 18 | EtOH | 127.2 | 0.3 | 40.9 | 0.8 | 113.1 | 1 | 22.7 | 0.4 |
| Formulation C | Inventive example 15 | EtOH | 129.3 | 1.6 | 37.6 | 0.7 | 123 | 3.3 | 22.5 | 1.3 |

INDUSTRIAL APPLICABILITY

The silicone-(meth)acrylate copolymer described herein shows excellent solubility with ethanol and thus enables free-radical polymerization directly in ethanol to prepare the copolymer. Without wishing to be bound by theory, it is thought that when ethanol is used in the method for preparing the copolymer, no extra solvent exchange is required for the copolymer solution, reducing manufacturing cost and streamlining the supply chain. Furthermore, it is thought that ethanol is ubiquitous in personal care applications, and ethanol is a commercially important bioderived carrier that may improve the sustainability profile of the overall copolymer solution as a product.

In addition, i) the (small) acrylate monomer is thought to relieve the steric hindrance and drives the quantitative conversion of other monomers, especially iii) the silicone-(meth)acrylate macro-monomer. The copolymerization of acrylates and methacrylates in general favors methacrylates, meaning methacrylates are often consumed first. However, the inventors found that the method of making the copolymer via free radical polymerization reduced the residual monomer to <500 ppm, alternatively <100 ppm, which may make the resulting copolymer suitable for personal care applications without an extra stripping and/or solvent exchange step in the method for preparing the copolymer and/or homogeneous solution thereof.

The copolymers described herein show excellent performance including water and sebum repellency as neat films and in exemplary foundation formulations. Surprisingly, iii) the silicone-(meth)acrylate macro-monomer content can be reduced to be as low as 20%, alternatively 20% to 30%, of the mixture of monomers used to prepare the copolymer, and the excellent water and sebum repellency of the copolymer produced are maintained, as shown by the inventive examples, above. Due to the relatively low amounts of iii) the silicone-(meth)acrylate macro-monomer, the formulation has reduced cost as compared to comparative compositions with higher amounts of silicone (meth)acrylate material. Furthermore, the formulation may contain more bio-derived monomers to improve the sustainability profile of the product as compared to comparative products containing higher amounts of silicone containing materials.

The invention claimed is:

1. A copolymer obtained by copolymerizing a mixture of monomers comprising:

i) 15 weight % to 45 weight %, based on combined weights of the monomers, of an acrylate monomer of formula

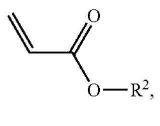

ii) 15 weight % to 40 weight %, based on combined weights of the monomers, of a (meth)acrylate monomer of formula

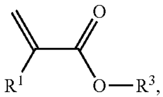

and iii) 20 weight % to 60 weight %, based on combined weights of the monomers, of an organosiloxane-(meth) acrylate macro-monomer of formula $XSi(R^4)_3$, where $R^1$ is selected from the group consisting of hydrogen and methyl, $R^2$ is a monovalent hydrocarbon group of 1 to 4 carbon atoms, $R^3$ is a monovalent hydrocarbon group of 8 to 13 carbon atoms, each X is a (meth) acryloxyalkyl group, each $R^4$ is selected from $—OSi(R^5)_3$ and R, with the proviso that at least two of $R^4$ are $—OSi(R^5)_3$; where each R is a monovalent hydrocarbon group; where each $R^5$ is selected from R, $-DSi(R^6)_3$, and $—[OSiR_2]_mOSiR_3$; where each $R^6$ is selected from R, $-DSi(R^7)_3$, and $—[OSiR_2]_mOSiR_3$; where each $R^7$ is selected from R, $-DSi(R^8)_3$, and $—[OSiR_2]_mO-SiR_3$; where each $R^8$ is selected from R and $—[OSiR_2]_mOSiR_3$; where each D is selected from oxygen and a divalent hydrocarbon group, and where $0 \leq m \leq 100$, and iv) 5 weight % to 20 weight %, based on combined weight of the monomers, of an itaconate ester monomer of formula

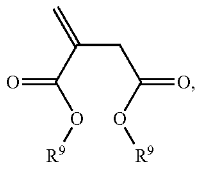

where each $R^9$ is an independently selected alkyl group of 1 to 8 carbon atoms, and where iv) the itaconate ester monomer comprises dibutyl itaconate.

2. The copolymer of claim 1, where iv) the itaconate ester monomer comprises dibutyl itaconate.

3. The copolymer of claim 1, where in the formula for i) the acrylate monomer $R^2$ is an alkyl group of 2 or 3 carbon atoms.

4. The copolymer of claim 3, where i) the acrylate monomer comprises ethyl acrylate.

5. The copolymer of claim 1, where in the formula for ii) the (meth)acrylate monomer, $R^1$ is methyl and $R^3$ is an alkyl group of 10 to 12 carbon atoms or a cycloalkyl group of 10 to 12 carbon atoms.

6. The copolymer of claim 5, where ii) the (meth)acrylate monomer is selected from the group consisting of lauryl methacrylate, isobornyl methacrylate, and a combination thereof.

7. The copolymer of claim 1, where iii) the macromonomer has formula:

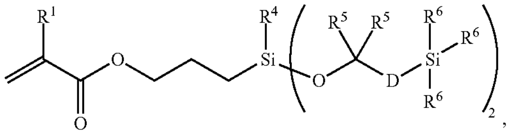

where $R^1$, $R^4$, $R^5$, $R^6$, and D are as described above.

8. The copolymer of claim 7, where iii) the macromonomer is selected from the group consisting of:

3-(5-((1,1,1,3,5,5,5-heptamethyltrisiloxan-3-yl)oxy)-1,1,1,3,7,9,9,9-octamethyl-3,7-bis((trimethylsilyl)oxy)pentasiloxan-5-yl)propyl methacrylate;

3-(1,5-bis(2-(1,1,1,5,5,5-hexamethyl-3-((trimethylsilyl)oxy)trisiloxan-3-yl)ethyl)-3-(((2-(1,1,1,5,5,5-hexamethyl-3-((trimethylsilyl)oxy)trisiloxan-3-yl)ethyl)dimethylsilyl)oxy)-1,1,5,5-tetramethyltrisiloxan-3-yl)propyl methacrylate;

and a combination thereof.

9. The copolymer of claim 1, where the mixture of monomers further comprises: v) >0 to 10 weight % of a small (meth)acrylate monomer of formula

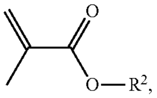

where $R^2$ is as described above.

10. A composition comprising: the copolymer of claim 1, and ethanol, wherein the copolymer is soluble in the ethanol, and the composition is a homogeneous solution.

11. A method for preparing the copolymer of claim 1, wherein the method comprises:

1) Copolymerizing the mixture of monomers in the presence of a radical initiator, and optionally a solvent; thereby forming a reaction mixture; and 2) quenching the reaction mixture.

12. The method of claim 11, further comprising 3) purifying the copolymer, and optionally 4) dissolving the copolymer in ethanol, and/or optionally 5) conducting a solvent exchange thereby dissolving the copolymer in a carrier selected from the group consisting of isopropyl alcohol, acetone, caprylic/capric triglycerides, isododecane, an alkane of 9 to 11 carbon atoms, a cyclic polydiorganosiloxane, a linear polydiorganosiloxane, or a combination of two or more thereof.

13. A method for preparing a personal care composition comprising adding the copolymer of claim 1 to the personal care composition.

14. The method of claim 13, where the composition is a foundation.

15. The method of claim 11, where step 1) is performed at a temperature>30° C.

16. The method of claim 11, where the solvent is added in step 1), and the solvent comprises a simple alcohol of formula $R^2OH$, where $R^2$ is a monovalent hydrocarbon group of 1 to 4 carbon atoms.

17. The method of claim 11, where step 2) is performed by cooling the reaction mixture to 25±5° C.

* * * * *